(12) United States Patent
Tachiya

(10) Patent No.: US 8,158,821 B2
(45) Date of Patent: Apr. 17, 2012

(54) CRYSTAL OF 5-AMINOLEVULINIC ACID PHOSPHATE AND PROCESS FOR PRODUCING THE SAME

(75) Inventor: Naohisa Tachiya, Satte (JP)

(73) Assignee: Cosmo Oil Co., Ltd., Tokyo (JP)

( * ) Notice: Subject to any disclaimer, the term of this patent is extended or adjusted under 35 U.S.C. 154(b) by 218 days.

(21) Appl. No.: 12/302,378

(22) PCT Filed: Jul. 24, 2007

(86) PCT No.: PCT/JP2007/064515
§ 371 (c)(1),
(2), (4) Date: Nov. 25, 2008

(87) PCT Pub. No.: WO2008/020532
PCT Pub. Date: Feb. 21, 2008

(65) Prior Publication Data
US 2010/0004477 A1  Jan. 7, 2010

(30) Foreign Application Priority Data

Aug. 15, 2006 (JP) ................................. 2006-221538

(51) Int. Cl.
*C07C 229/08* (2006.01)
(52) U.S. Cl. ...................................................... 562/567
(58) Field of Classification Search ................ None
See application file for complete search history.

(56) References Cited

U.S. PATENT DOCUMENTS 5,368,841 A  11/1994 Trauner et al.

FOREIGN PATENT DOCUMENTS

| EP | 1731500 A1 | 12/2006 |
|---|---|---|
| JP | 4-9360 A | 1/1992 |
| JP | 4-217650 A | 8/1992 |
| JP | 7-188133 A | 7/1995 |
| JP | 2006-182753 * | 7/2006 |
| JP | 2006-182753 A | 7/2006 |
| JP | 2007-15937 A | 1/2007 |
| WO | 2005/092838 A1 | 10/2005 |
| WO | 2005/100300 A1 | 10/2005 |

OTHER PUBLICATIONS

Machine translation of JP 2006-182753. Accessed Dec. 8, 2009.*
Brittain et al. "Polymorphism in Pharmaceutical Dosage Forms." Polymorphism in Pharmaceutical Solids XX (Jan. 1999), relevant pages attached.*
Morissette et al. Advanced Drug Delivery Reviews 2004, 56, 275-300.*
Vippagunta et al. Advanced Drug Delivery Reviews 2001, 48, 3-26, abstract.*
Peter, W. et al., J. Am. Acad. Dermatol., 31, pp. 678-680 (1994).
Hillemanns, P. et. al., Int. J. Cancer, vol. 85, pp. 649-653 (2000).
Kamasaki et al., Journal of Japan Society for Laser Medicine, vol. 22, pp. 255-262 (2001).
Office Action dated Jun. 30, 2011, issued in counterpart Australian Application No. 2007285257.
Russian Office Action, dated Nov. 16, 2010 issued from the Russian Patent Office in a counterpart application No. 2008150498/04(066322) and an English language translation thereof.
Extended European Search Report, issued Jul. 15, 2011, in corresponding European Patent Application No. 07791240.0.
Japanese Office Action issued Nov. 10, 2011 in corresponding Japanese Patent Application No. 2006-221538.
Bryn et al., "Solid-State Pharmaceutical Chemistry," Chem. Mater., 1994, 6, pp. 1148-1158.
Office Action dated Oct. 31, 2011 from the State Intellectual Property Office of P.R.C. in counterpart Chinese application No. 200780022901.9.
Office Action dated Oct. 5, 2011 from the israeli Patent Office in counterpart Israeli application No. 194938.
European Office Action issued on Dec. 13, 2011 from European Patent Office in a counterpart European Application No. 07791240.0.

* cited by examiner

*Primary Examiner* — Rebecca Anderson
*Assistant Examiner* — Alicia L Otton
(74) *Attorney, Agent, or Firm* — Sughrue Mion, PLLC

(57) ABSTRACT

To provide a novel crystal of 5-aminolevulinic acid phosphate having a high thermal stability, a high melting point, and an excellent moisture absorption resistance as well as a process for producing the same. A crystal of 5-aminolevulinic acid phosphate, which shows characteristic peaks at 7.9°±0.2°, 15.8°±0.2°, 18.9°±0.2°, 20.7°±0.2°, 21.1°±0.2°, 21.4°±0.2°, 22.9°±0.2°, 33.1°±0.2°, and 34.8±0.2° as diffraction angles 2θ in a powder X-ray diffraction, and a process for producing the same.

4 Claims, 1 Drawing Sheet

CRYSTAL OF 5-AMINOLEVULINIC ACID PHOSPHATE AND PROCESS FOR PRODUCING THE SAME

TECHNICAL FIELD

The present invention relates to a novel crystal of 5-aminolevulinic acid phosphate useful in the fields of medical care, agriculture, cosmetic treatment, and the like as well as a process for producing the same.

BACKGROUND ART

With regard to 5-aminolevulinic acid, various uses have been proposed in various fields. For example, the compound is known to be useful for $VB_{12}$ production, heme enzyme production, microbial culturing, porphyrin production and the like in the field of microbes/fermentation, for infectious disease treatment (Non-Patent Document 1), sterilization, Haemophilus diagnosis, derivative materials, depilation, rheumatism therapy (Non-Patent Document 2), cancer therapy (Non-Patent Document 3), thrombus therapy (Non-Patent Document 4), diagnosis during cancer operation (Non-Patent Document 5), animal cell culture, UV cut, heme metabolism research, hair care, diagnosis of heavy metal poisoning and porphyria, anemia prevention, and the like in the field of animal/medical care, and for agricultural chemicals and the like in the field of plants.

5-Aminolevulinic acid phosphate which is phosphate of the acid is found as a substance which overcomes problems in hydrochloride thereof which has been only known as the salt until that time and exhibits excellent effects such as odorless, low irritation, and high permeability into skin, so that the phosphate is suitable for transdermal administration and oral administration and also is useful as a photodynamic therapy and a photodynamic diagnostic agent (Patent Document 1). In Patent Document 1, 5-aminolevulinic acid phosphate was obtained as a solid precipitated by eluting 5-aminolevulinic acid adsorbed on an ion-exchange resin with aqueous ammonia, adding phosphoric acid to the resultant eluate, and then adding acetone thereto. It is also disclosed in Patent Document 2 that 5-aminolevulinic acid phosphate has properties suitable for the use of a photochemical therapy.

The agents such as pharmaceuticals and agricultural chemicals are frequently constrained to be stored for a long period of time and sometimes absorb moisture from the atmosphere during the storage. As a result, degradation occurs and thus a certain quality as pharmaceuticals and agricultural chemicals cannot be maintained, so that a high moisture absorption resistance is required. Moreover, there are many cases where heat sterilization is necessary and hence a high stability against heat treatment is also required.

Patent Document 1: WO2005/100300 pamphlet
Patent Document 2: WO2005/092838 pamphlet
Non-Patent Document 1: Peter W. et al., J. Am. Acad. Dermatol., 31, 678-680 (1994)
Non-Patent Document 2: Kenneth T., U.S. Pat. No. 5,368,841 (1994)
Non-Patent Document 3: Hillemanns P. et al., Int. J. Cancer, 85, 649-653 (2000)
Non-Patent Document 4: Ichiro Yamada et al., Abstracts of Papers, China-Japan Congress of Plastic Surgery (1988)
Non-Patent Document 5: Kamasaki N. et al., Journal of Japan Society for Laser Medicine, 22, 255-262 (2001)

DISCLOSURE OF THE INVENTION

Problems that the Invention is to Solve

However, 5-aminolevulinic acid phosphate hitherto known has a melting point of only a little over 100° C. and is not resistant to common heating sterilization at 121° C. Moreover, when heated, the phosphate is converted into a dimer of 5-aminolevulinic acid molecules to form 2,5-pyrazinedipropionic acid (PDPA), resulting in an impurity-containing one. Furthermore, the phosphate showed a high moisture-absorbing property.

Accordingly, an object of the invention is to provide a novel crystal of 5-aminolevulinic acid phosphate having a high thermal stability, a high melting point, and an excellent moisture absorption resistance as well as a process for producing the same.

Means for Solving the Problems

Under such a situation, the present inventors have found that a novel crystal of 5-aminolevulinic acid phosphate solves the above problems.

Namely, the invention provides a crystal of 5-aminolevulinic acid phosphate, which shows characteristic peaks at 7.9°±0.2°, 15.8°±0.2°, 18.9°±0.2°, 20.7°±0.2°, 21.1°±0.2°, 21.4°+±0.2°, 22.9°±0.2°, 33.1°±0.2°, and 34.8±0.2° as diffraction angles 2θ in a powder X-ray diffraction.

Moreover, the invention provides a process for producing the above crystal, wherein a solid of 5-aminolevulinic acid phosphate is dissolved in a solvent and then a poor solvent is added thereto to precipitate the crystal.

Furthermore, the invention provides a process for producing the above crystal, wherein 5-aminolevulinic acid or a salt thereof, phosphoric acid, and a basic nitrogen-containing compound are dissolved in a solvent and then a poor solvent is added thereto to precipitate the crystal.

Advantage of the Invention

The crystal of 5-aminolevulinic acid phosphate of the invention has a high melting point and an excellent moisture absorption resistance and also is remarkably little in the content of the impurity (PDPA) to be formed by heating and thus excellent in thermal stability, so that the crystal is useful as an active ingredient for pharmaceuticals, agricultural chemicals, and the like which may undergo long-term storage and heating sterilization. In addition, according to the production process of the invention, such a novel crystal can be produced.

BEST MODE FOR CARRYING OUT THE INVENTION

Figure 1:
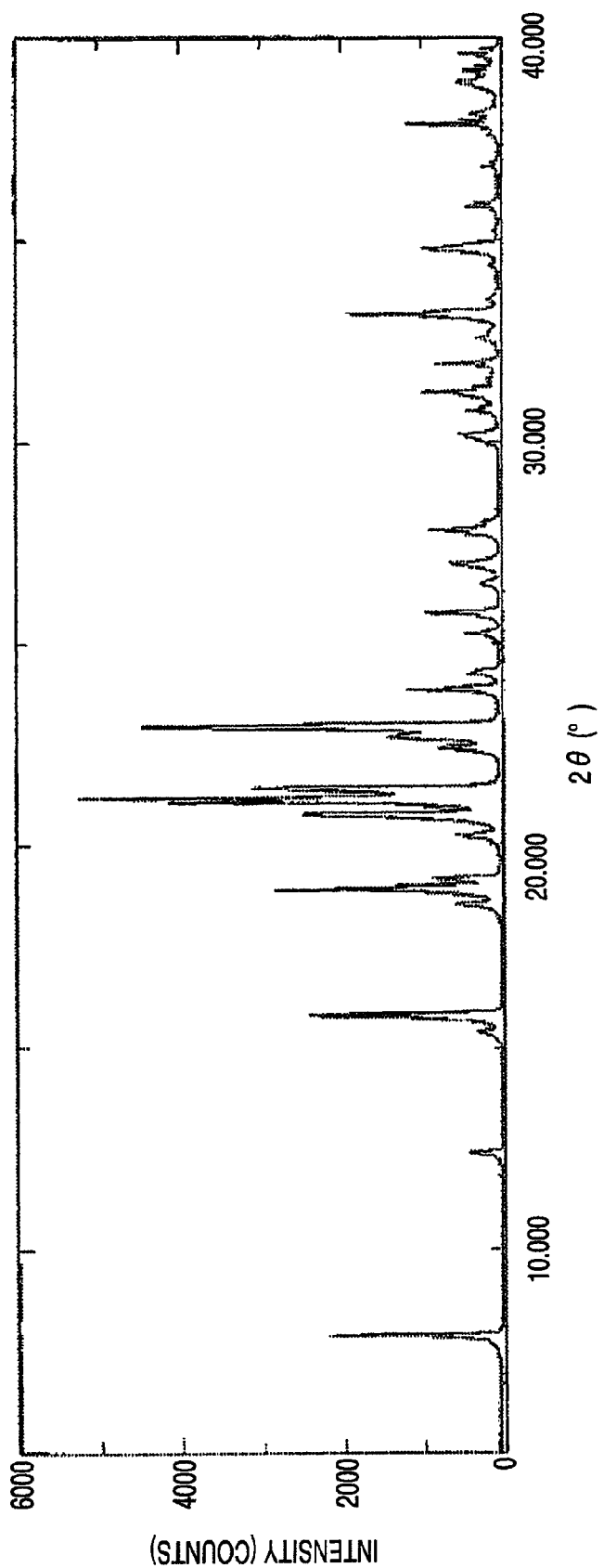
FIG. 1 It is a drawing showing a powder X-ray diffraction spectrum of the crystal obtained in Example 1.

The crystal of the invention shows characteristic peaks at 7.9°±0.2°, 15.8°±0.2°, 18.9°+0.2°, 20.7°±0.2°, 21.1°±0.2°, 21.4°±0.2°, 22.9°±0.2°, 33.1°±0.2°, and 34.8±0.2° as diffraction angles 2θ in a powder X-ray diffraction. The "±0.2°" in the values of these characteristic peaks is an error of measurement derived from measuring conditions such as a measuring apparatus and conditions for reading the peaks, and the error is preferably ±0.1°, more preferably ±0.01°. The measurement of the diffraction angles 2θ by powder X-ray diffraction is carried out under the following measuring conditions.

Apparatus: a rotary anticathode-type X-ray diffraction apparatus RINT2500V manufactured by Rigaku Corporation
X-ray: Cu/tube voltage 50 kV/tube current 40 mA
Goniometer: RINT2000 vertical goniometer
Attachment: 5 sample changer
Filter: not used
Incident monochrome: not used
Counter monochromator: fully automatic monochromator
Divergence slit: 1°
Scattering slit: 1°
Receiving slit: 0.15 mm
Monochrome receiving slit: 0.8 mm
Counter: scintillation counter (SC50)
Scanning mode: continuous
Scanning speed: 4.000°/min
Sampling width: 0.0200
Scanning axis: 2θ/θ
Scanning range: 5.000 to 40.000°
θ offset: 0.000°

Incidentally, these peaks can be observed by a common powder X-ray diffraction apparatus to which a monochromator is mounted but, in an apparatus with a bad resolution, e.g., an apparatus wherein a monochromator is not mounted, there is a case where a peak position becomes unclear due to overlap with a noise peak. Moreover, in the case where scanning speed is high or the apparatus is set in a state of a wide receiving slit, adjacent peaks become broad and are sometimes overlapped.

The crystal of the invention can be obtained by dissolving a solid of 5-aminolevulinic acid phosphate in a solvent and then adding a poor solvent to precipitate the crystal.

The solid of 5-aminolevulinic acid phosphate to be used may be one containing 5-aminolevulinic acid phosphate as a main ingredient and is not necessarily a crystal. The solid can be obtained by the method described in Example 1 of WO2005/100300 pamphlet. Specifically, the solid was obtained as a solid precipitated by adsorbing a 5-aminolevulinic acid salt such as 5-aminolevulinic acid hydrochloride on an ion-exchange resin, subsequently eluting it with a basic solvent such as aqueous ammonia, adding phosphoric acid to the resultant eluate, concentrating the thus obtained solution as needed, adding a poor solvent such as acetone thereto, and allowing the whole to stand after stirring as needed.

The purity of the solid is not particularly limited but is preferably 50% by mass or more, more preferably 60% by mass or more, particularly preferably 70% by mass or more. Furthermore, it is preferably 70 to 99.9% by mass, particularly 80 to 99.9% by mass, among others, 90 to 99.9% by mass.

As the solvent for dissolving the above solid, the solvent is not particularly limited so far as it is a hydrophilic solvent but is preferably water or an alcohol, more preferably water, methanol, ethanol, n-propanol, or isopropanol, and water is particularly preferred.

The amount of the solid of 5-aminolevulinic acid phosphate to be added to the solvent is not limited so far as the solid is dissolved. From the efficiency of crystal precipitation at the time when a poor solvent is added, the amount is 10 to 70% by mass, particularly 30 to 60% by mass based on the total amount of the solvent.

The solution obtained by dissolving the above solid in the solvent is preferably a solution containing 5-aminolevulinic acid phosphate in high purity and specifically, it is preferred that, of the substances other than the solvent, 5-aminolevulinic acid phosphate accounts for 70 to 99.9% by mass, furthermore 80 to 99.9% by mass, particularly 90 to 99.9% by mass.

As the poor solvent to be added, there may be mentioned methanol, ethanol, n-propanol, isopropanol, acetone, γ-butyrolactone, 1,4-dioxane, methoxyethanol, tetraethylene glycol dimethyl ether, and triethylene glycol dimethyl ether by way of examples. As suitable combinations of the solvent/the poor solvent, there may be mentioned water/methanol, water/ethanol, water/isopropanol, methanol/ethanol, and methanol/isopropanol by way of examples.

The temperature of both liquids at the time when the poor solvent is added to the solution obtained by dissolving the solid in the solvent is particularly not limited so far as freezing of the liquids does not occur, but energy efficiency decreases when the temperature is elevated, so that the temperature is preferably −30° C. to 80° C.

The volume of the poor solvent to be added is not categorically determined depending on the concentration and kind of the solid of 5-aminolevulinic acid phosphate dissolved and can be determined with confirming a precipitation state until the solid is precipitated. For example, the volume may be preferably 5 to 20 mass equivalents to the amount of 5-aminolevulinic acid phosphate in the solvent.

After the addition of the poor solvent, the whole is preferably stirred and allowed to stand. The stirring time can be, for example, 5 minutes to 30 minutes. The standing time can be, for example, 5 minutes to 15 days.

Moreover, the production of the crystal of the invention can be also achieved by dissolving 5-aminolevulinic acid or a salt thereof, phosphoric acid, and a basic nitrogen-containing compound in a solvent and then adding a poor solvent to the resultant solution to precipitate the crystal.

As the salt of 5-aminolevulinic acid to be used in the method, there may be mentioned hydrochloride, hydrobromide, sulfonate, sulfate, and nitrate, preferably hydrochloride. They can be obtained by any known method and, for example, can be obtained by the methods described in, for example, JP-A-48-92328, JP-A-2005-314360, JP-A-2005-314361, and JP-A-2006-182753.

The amount of 5-aminolevulinic acid or the salt thereof to be dissolved in the solvent is preferably 10 to 90% by mass, particularly 20 to 70% by mass, based on the solvent.

Moreover, the basic nitrogen-containing compound to be used in the method is not particularly limited but a pyridine and an amine may be mentioned and, of these, an amine is preferred.

As the pyridine to be used, a compound represented by the following formula (1):

[Chem 1]

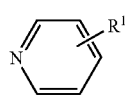

(1)

(wherein $R^1$ represents a hydrogen atom, a hydrocarbon group having 1 to 40 carbon atoms which may have a substituent, or an amino group which may have a substituent) is preferred.

As the hydrocarbon group, an alkyl group and an aralkyl group may be mentioned. As the alkyl group, a linear, branched, or cyclic alkyl group may be mentioned and the alkyl group having 1 to 40, further 1 to 18, particularly 1 to 7 carbon atoms is preferred.

Moreover, as the alkyl group constituting the aralkyl group, a linear, branched, or cyclic alkyl group may be mentioned and the alkyl group having 1 to 40, further 1 to 18, particularly 1 to 7 carbon atoms is preferred. As the aryl group constituting the aralkyl group, an aryl group having 6 to 20 carbon atoms may be mentioned.

As preferred alkyl group having 1 to 18 carbon atoms, there may be, for example, mentioned a methyl group, an ethyl group, an n-propyl group, an isopropyl group, an n-butyl group, an isobutyl group, a tert-butyl group, an n-pentyl group, an isopentyl group, a neopentyl group, a tert-pentyl group, a 2-methylbutyl group, an n-hexyl group, an isohexyl group, a 3-methylpentyl group, an ethylbutyl group, an n-heptyl group, a 2-methylhexyl group, an n-octyl group, an isooctyl group, a tert-octyl group, a 2-ethylhexyl group, a 3-methylheptyl group, an n-nonyl group, an isononyl group, a 1-methyloctyl group, an ethylheptyl group, an n-decyl group, a 1-methylnonyl group, an n-undecyl group, a 1,1-dimethylnonyl group, an n-dodecyl group, an n-tridecyl group, an n-tetradecyl group, an n-pentadecyl group, an n-hexadecyl group, an n-heptadecyl group, an n-octadecyl group, and the like.

As more preferred alkyl group having 1 to 7 carbon atoms, there may be, for example, mentioned a methyl group, an ethyl group, an n-propyl group, an isopropyl group, an n-butyl group, an isobutyl group, a tert-butyl group, an n-pentyl group, an isopentyl group, a neopentyl group, a tert-pentyl group, a 2-methylbutyl group, an n-hexyl group, an isohexyl group, a 3-methylpentyl group, an ethylbutyl group, an n-heptyl group, and a 2-methylhexyl group.

As preferred alkyl group having 1 to 18 carbon atoms constituting the aralkyl group, there may be, for example, mentioned a methyl group, an ethyl group, an n-propyl group, an isopropyl group, an n-butyl group, an isobutyl group, a tert-butyl group, an n-pentyl group, an isopentyl group, a neopentyl group, a tert-pentyl group, a 2-methylbutyl group, an n-hexyl group, an isohexyl group, a 3-methylpentyl group, an ethylbutyl group, an n-heptyl group, a 2-methylhexyl group, an n-octyl group, an isooctyl group, a tert-octyl group, a 2-ethylhexyl group, a 3-methylheptyl group, an n-nonyl group, an isononyl group, a 1-methyloctyl group, an ethylheptyl group, an n-decyl group, a 1-methylnonyl group, an n-undecyl group, a 1,1-dimethylnonyl group, an n-dodecyl group, an n-tridecyl group, an n-tetradecyl group, an n-pentadecyl group, an n-hexadecyl group, an n-heptadecyl group, an n-octadecyl group, and the like.

As preferred alkyl group having 1 to 7 carbon atoms constituting the aralkyl group, there may be, for example, mentioned a methyl group, an ethyl group, an n-propyl group, an isopropyl group, an n-butyl group, an isobutyl group, a tert-butyl group, an n-pentyl group, an isopentyl group, a neopentyl group, a tert-pentyl group, a 2-methylbutyl group, an n-hexyl group, an isohexyl group, a 3-methylpentyl group, an ethylbutyl group, an n-heptyl group, and a 2-methylhexyl group.

As the aryl group having 6 to 20 carbon atoms constituting the aralkyl group, there may be, for example, mentioned a phenyl group, a naphthyl group, an anthryl group, a phenanthryl group, and the like, and a phenyl group is preferred.

As preferred aralkyl group, there may be mentioned a benzyl group and a phenethyl group.

As the substituent which the hydrocarbon of $R^1$ may have, there may be mentioned a group selected from a hydroxyl group, an alkoxy group, an acyloxy group, an alkoxycarbonyloxy group, an amino group, an aryl group, an oxo group, a fluoro group, a chloro group, and a nitro group. As the alkoxy group, an alkoxy group having 1 to 18 carbon atoms, particularly an alkoxy group having 1 to 7 carbon atoms is preferred. As the acyloxy group, an alkanoyloxy group having 1 to 18 carbon atoms, particularly an alkanoyloxy group having 2 to 8 carbon atoms is preferred. As the alkoxycarbonyloxy group, a $C_{1-18}$ alkoxy-carbonyloxy group, particularly a $C_{1-7}$ alkoxy-carbonyloxy group is preferred.

As the substituent in the amino group which may have a substituent, there may be mentioned an alkyl group having 1 to 18 carbon atoms, an aryl group having 6 to 16 carbon atoms, and an aralkyl group having 7 to 20 carbon atoms. An alkyl group having 1 to 6 carbon atoms is more preferred, and a methyl group, an ethyl group, or a propyl group is particularly preferred.

As preferred pyridines, there may be mentioned pyridine, α-picoline, β-picoline, γ-picoline, and 4-dimethylaminopyridine.

Moreover, as the amine to be used, an amine represented by the following formula (2)

$$NH_m R^2{}_{3-m} \qquad (2)$$

(wherein m represents an integer of 0 to 3 and $R^2$ represents a hydrogen atom or a hydrocarbon group having 1 to 40 carbon atoms which may have a substituent) is preferred.

As the hydrocarbon group, an alkyl group, an aralkyl group, and an aryl group may be mentioned. As the alkyl group, a linear, branched, or cyclic alkyl group may be mentioned, and the alkyl group having 1 to 40, further 1 to 18, particularly 1 to 7 carbon atoms is preferred. As the aralkyl group, an aralkyl group having 7 to 26 carbon atoms may be mentioned. Moreover, as the aryl group, an aryl group having 6 to 20 carbon atoms may be mentioned.

As preferred alkyl groups having 1 to 18 carbon atoms, there may be, for example, mentioned a methyl group, an ethyl group, an n-propyl group, an isopropyl group, an n-butyl group, an isobutyl group, a tert-butyl group, an n-pentyl group, an isopentyl group, a neopentyl group, a tert-pentyl group, a 2-methylbutyl group, an n-hexyl group, an isohexyl group, a 3-methylpentyl group, an ethylbutyl group, an n-heptyl group, a 2-methylhexyl group, an n-octyl group, an isooctyl group, a tert-octyl group, a 2-ethylhexyl group, a 3-methylheptyl group, an n-nonyl group, an isononyl group, a 1-methyloctyl group, an ethylheptyl group, an n-decyl group, a 1-methylnonyl group, an n-undecyl group, a 1,1-dimethylnonyl group, an n-dodecyl group, an n-tridecyl group, an n-tetradecyl group, an n-pentadecyl group, an n-hexadecyl group, an n-heptadecyl group, an n-octadecyl group, and the like.

As more preferred alkyl groups having 1 to 7 carbon atoms, there may be, for example, mentioned a methyl group, an ethyl group, an n-propyl group, an isopropyl group, an n-butyl group, an isobutyl group, a tert-butyl group, an n-pentyl group, an isopentyl group, a neopentyl group, a tert-pentyl group, a 2-methylbutyl group, an n-hexyl group, an isohexyl group, a 3-methylpentyl group, an ethylbutyl group, an n-heptyl group, and a 2-methylhexyl group.

As these alkyl groups, a methyl group, an ethyl group, an n-propyl group, an isopropyl group, an n-butyl group, an isobutyl group, a tert-butyl group, an n-pentyl group, and an isopentyl group are preferred.

As the aralkyl group having 7 to 26 carbon atoms, one constituted by an alkyl group having 1 to 6 carbon atoms and an aryl group having 6 to 20 carbon atoms is preferred. As the alkyl group having 1 to 6 carbon atoms, there may be mentioned a methyl group, an ethyl group, an n-propyl group, an isopropyl group, an n-butyl group, an isobutyl group, a tert-butyl group, an n-pentyl group, an n-hexyl group, a cyclopropyl group, a cyclobutyl group, a cyclohexyl group, and the like. As the aryl group having 6 to 20 carbon atoms, there may be mentioned a phenyl group, a naphthyl group, and the like. Of aralkyl groups having 7 to 26 carbon atoms, a benzyl group, a phenethyl group, or a 9-fluorenylmethyl group is preferred, and a benzyl group or a phenethyl group is particularly preferred.

As the aryl group having 6 to 20 carbon atoms, there may be mentioned a phenyl group, a naphthyl group, and the like, and a phenyl group is preferred.

As the substituent which the hydrocarbon of $R^2$ may have, there may be mentioned a group selected from a hydroxyl group, an alkoxy group, an acyloxy group, an alkoxycarbonyloxy group, an amino group, an aryl group, an oxo group, a fluoro group, a chloro group, and a nitro group. As the alkoxy group, an alkoxy group having 1 to 18 carbon atoms, particularly an alkoxy group having 1 to 7 carbon atoms is preferred. As the acyloxy group, an alkanoyloxy group having 1 to 18 carbon atoms, particularly an alkanoyloxy group having 2 to 8 carbon atoms is preferred. As the alkoxycarbonyloxy group, a $C_{1-18}$ alkoxy-carbonyloxy group, particularly a $C_{1-7}$ alkoxy-carbonyloxy group is preferred.

As preferred amines, there may be, for example, mentioned ammonia, methylamine, dimethylamine, trimethylamine, ethylamine, diethylamine, triethylamine, n-propylamine, di-n-propylamine, tri-n-propylamine, isopropylamine, diisopropylamine, triisopropylamine, n-butylamine, di-n-butylamine, tri-n-butylamine, and aniline. Of these, triethylamine is preferred.

The amount of phosphoric acid to be used is not particularly limited so far as the amount is 1 molar equivalent or more to that of 5-aminolevulinic acid or a salt thereof but the amount is usually 1 to 20 molar equivalents, preferably 1 to 5 molar equivalents, more preferably 1 to 1.5 molar equivalents. Moreover, the amount of phosphoric acid to be dissolved in the solvent is 1 to 10% by mol, particularly 2 to 8% by mol.

The amount of the basic nitrogen-containing compound is not particularly limited. In the case where an amine which has not formed a salt is used as a reaction raw material, a preferred amount of the basic nitrogen-containing compound is usually 0.01 to 20 molar equivalents, preferably 0.1 to 5 molar equivalent, more preferably 1 to 2 molar equivalents, particularly preferably 1 to 1.5 molar equivalents.

In the case where an amine which has formed a salt is used as the basic nitrogen-containing compound, a preferred mixing amount of the amine is usually 0.1 to 50 molar equivalents, preferably 1 to 5 molar equivalents, more preferably 1 to 2 equivalents. Moreover, the amount of the basic nitrogen-containing compound to be dissolved in the solvent is 1 to 10% by mol, particularly 2 to 8% by mol based on the solvent.

The method of dissolving 5-aminolevulinic acid or a salt thereof, phosphoric acid, and the basic nitrogen-containing compound is not particularly limited but it is preferred to form a homogeneous solution by stirring. Particularly, in the case where a 5-aminolevulinic acid salt is used as a raw material, ion-exchange takes place to form 5-aminolevulinic acid phosphate and also an ammonium-type salt is formed between the basic nitrogen-containing compound and the acid which was incorporated to 5-aminolevulinic acid. In that case, it is desirable to carry out a sufficient reaction prior to the addition of the poor solvent.

The solvent dissolving them is not particularly limited so far as it is a hydrophilic solvent but is preferably water or an alcohol, more preferably water, methanol, ethanol, n-propanol, or isopropanol.

In the resultant solution, 5-aminolevulinic acid phosphate is formed by the reaction. The reaction temperature is not particularly limited unless freezing of the solution or dryness of the content takes place. However, since exothermic heat may be frequently generated when the basic nitrogen-containing compound is allowed to act, it is preferred to regulate the resultant solution to −30° C. to 30° C. Moreover, from the viewpoint of efficiency of the reaction, the reaction time is preferably 1 minute to 24 hours, and a reaction time of 10 minutes to 2 hours is preferred.

In this connection, the acid which originally formed a salt with 5-aminolevulinic acid reacts with the added basic nitrogen-containing compound to form precipitate in some cases during the reaction but the precipitate formation does not particularly influence the reaction. After the completion of the reaction, the crystal of 5-aminolevulinic acid phosphate can be precipitated by adding a solvent having lower solubility for 5-aminolevulinic acid phosphate. On that occasion, the impurity salt usually dissolves although it depends on the kind and amount of the solvent used in the reaction and the kind and amount of the solvent used in the precipitation.

By adding to the resultant solution a poor solvent which is a solvent having a low solubility for 5-aminolevulinic acid phosphate as compared with the solvent used in the reaction, the crystal of the invention is precipitated. As the poor solvent to be added, there may be mentioned methanol, ethanol, n-propanol, isopropanol, acetone, γ-butyrolactone, 1,4-dioxane, methoxyethanol, tetraethylene glycol dimethyl ether, and triethylene glycol dimethyl ether by way of examples.

The amount of the poor solvent to be used may be suitably regulated depending on the kind thereof and the kind and amount of the reaction solvent but, for example, may be 0.5 to 10 mass equivalents, preferably 1.5 to 8 mass equivalents to the total amount of the solution obtained by dissolving 5-aminolevulinic acid or a salt thereof, phosphoric acid, and the basic nitrogen-containing compound in the solvent.

As preferred combination of the solvent/the poor solvent, there may be mentioned water/methanol, water/ethanol, water/isopropanol, methanol/ethanol, and methanol/isopropanol by way of examples.

After the addition of the poor solvent, the resultant mixture is preferably stirred and allowed to stand, if necessary. The standing time is, for example, 0.5 to 24 hours. On this occasion, the temperature is preferably 20 to 30° C.

In the production process, it is preferred to add the crystal of 5-aminolevulinic acid phosphate after the addition of the poor solvent or during the addition in view of the increase in efficiency of crystal precipitation. The amount of the crystal of 5-aminolevulinic acid phosphate to be added may be suitably regulated but is usually 0 to 10% by mass, preferably 0.01 to 5% by mass, more preferably 0.01 to 0.1% by mass based on the starting 5-aminolevulinic acid or a salt thereof.

The crystal of the invention obtained by precipitation by the above method as a precipitate can be collected by a common crystal-collecting method such as filtration. After collection, the crystal may be isolated by drying under reduced pressure.

Since the crystal of the invention has a high melting point, a high thermal stability, and an excellent moisture absorption resistance, a pharmaceutical composition using the same can be stored for a long period of time and can be subjected to usual heating sterilization at 121° C. In such a pharmaceutical composition, pharmacologically acceptable carriers such as water, a binder, a disintegrator, a dissolution accelerator, a lubricant, a filler, and an excipient can be incorporated. As agent forms, there may be mentioned a skin external preparation, a preparation for injection, a preparation for oral use, a suppository, and the like.

EXAMPLES

The following will describe the invention further in detail with reference to Examples but the invention is not limited thereto.

Example 1

Production of Crystal of 5-Aminolevulinic Acid Phosphate

In 14 g of purified water were dissolved 4.67 g (27.92 mmol) of 5-aminolevulinic acid hydrochloride and 3.576 g (31.33 mmol) of 85% by mass phosphoric acid, and then 2.970 g (29.35 mmol) of triethylamine was added dropwise under stirring at 0 to 5° C. After the completion of the dropwise addition, the whole was stirred at room temperature for 30 minutes and then 14.75 g of ethanol was added. In this state, when 1.01 mg of the crystal of 5-aminolevulinic acid phosphate (obtained in the following Example 2) was added and slow stirring was continued, a colorless transparent crystal was gradually begun to precipitate. After about 30 minutes of stirring, 59.07 g of ethanol was additionally added and the crystal was completely precipitated. The crystal was collected by suction filtration and dried under reduced pressure at room temperature for 16 hours. Thus, 5.742 g (25.07 mmol) of a crystal of 5-aminolevulinic acid phosphate was obtained in a yield of 90% by mol. The purity of the resultant crystal was 99.4% by mass.

$^1$H-NMR (D$_2$O, 400 MHz) δ ppm: 2.67 (t, 2H, CH$_2$), 2.86 (t, 2H, CH$_2$), 4.08 (s, 2H, CH$_2$). $^{13}$C-NMR (D$_2$O, 100 MHz) δ ppm: 30 (CH$_2$), 37 (CH$_2$), 50 (CH$_2$), 180 (CO), 207 (COO).

Content of PO$_4^{3-}$ determined by ion chromatography:

Theoretical value: 41.45%

Found value: 41%

Analytical conditions for ion chromatography: separation column: IonPac AS12A manufactured by Nippon Dionex, eluent: an aqueous solution containing Na$_2$CO$_3$ and NaHCO$_3$ (Na$_2$CO$_3$: 3.0 mmol/L, NaHCO$_3$: 0.5 mmol/L), flow rate: 1.5 mL/min., injected amount of sample: 25 μL, column temperature: 35° C., detector: electric conductivity detector.

A powder X-ray diffraction spectrum of the resultant crystal was measured under the following conditions described below. The results are shown in Table 1 and FIG. 1.

Apparatus: a rotary anticathode-type X-ray diffraction apparatus RINT2500V manufactured by Rigaku Corporation
X-ray: Cu/tube voltage 50 kV/tube current 40 mA
Goniometer: RINT2000 vertical goniometer
Attachment: 5 sample changer
Filter: not used
Incident monochrome: not used
Counter monochromator: fully automatic monochromator
Divergence slit: 1°
Scattering slit: 1°
Receiving slit: 0.15 mm
Monochrome receiving slit: 0.8 mm
Counter: scintillation counter (SC50)
Scanning mode: continuous
Scanning speed: 4.000°/min
Sampling width: 0.020°
Scanning axis: 2θ/θ
Scanning range: 5.000 to 40.000°
θ offset: 0.000°

TABLE 1

| Peak number | 2θ | d value | Intensity | Relative intensity |
|---|---|---|---|---|
| 1 | 7.900 | 11.1820 | 1593 | 42 |
| 2 | 12.380 | 7.1438 | 340 | 9 |
| 3 | 15.400 | 5.7490 | 267 | 7 |
| 4 | 15.800 | 5.6043 | 2033 | 53 |
| 5 | 18.520 | 4.7869 | 539 | 14 |
| 6 | 18.900 | 4.6915 | 2345 | 61 |
| 7 | 19.160 | 4.6284 | 744 | 20 |
| 8 | 20.220 | 4.3881 | 518 | 14 |
| 9 | 20.740 | 4.2792 | 2378 | 62 |
| 10 | 21.120 | 4.2031 | 3880 | 100 |
| 11 | 21.400 | 4.1487 | 2591 | 67 |
| 12 | 22.420 | 3.9622 | 731 | 19 |
| 13 | 22.700 | 3.9140 | 1352 | 35 |
| 14 | 22.940 | 3.8736 | 3821 | 99 |
| 15 | 23.860 | 3.7263 | 830 | 22 |
| 16 | 24.280 | 3.6628 | 348 | 9 |
| 17 | 25.240 | 3.5256 | 356 | 10 |
| 18 | 25.760 | 3.4556 | 619 | 16 |
| 19 | 26.500 | 3.3607 | 266 | 7 |
| 20 | 26.960 | 3.3044 | 570 | 15 |
| 21 | 27.820 | 3.2042 | 758 | 20 |
| 22 | 28.020 | 3.1818 | 227 | 6 |
| 23 | 30.180 | 2.9588 | 488 | 13 |
| 24 | 30.780 | 2.9025 | 314 | 9 |
| 25 | 31.240 | 2.8608 | 695 | 18 |
| 26 | 31.560 | 2.8325 | 166 | 5 |
| 27 | 31.940 | 2.7997 | 415 | 11 |
| 28 | 32.560 | 2.7477 | 261 | 7 |
| 29 | 32.740 | 2.7331 | 151 | 4 |
| 30 | 33.140 | 2.7010 | 1487 | 39 |
| 31 | 33.520 | 2.6712 | 164 | 5 |
| 32 | 34.360 | 2.6078 | 138 | 4 |
| 33 | 34.780 | 2.5773 | 900 | 24 |
| 34 | 35.820 | 2.5048 | 249 | 7 |
| 35 | 36.800 | 2.4403 | 133 | 4 |
| 36 | 37.620 | 2.3890 | 152 | 4 |
| 37 | 37.860 | 2.3744 | 676 | 18 |
| 38 | 38.120 | 2.3588 | 362 | 10 |
| 39 | 38.900 | 2.3133 | 518 | 14 |
| 40 | 39.180 | 2.2974 | 335 | 9 |
| 41 | 39.600 | 2.2740 | 315 | 9 |

Example 2

Production of Crystal of 5-Aminolevulinic Acid Phosphate

In 10 mL of purified water was dissolved 5 g of a solid (powder) (purity 96.0% by mass, the same shall apply hereinafter) of 5-aminolevulinic acid phosphate obtained by a conventional method (the method described in Example 1 of WO2005/100300 pamphlet), and then 100 mL of methanol was added under stirring. After 5 minutes of stirring at room temperature, the whole was allowed to stand at 4° C. for 14 hours. The precipitated crystal was collected and washed with 50 mL of acetone. It was dried under reduced pressure for 4 hours and 3.67 g of the crystal was collected. When powder X-ray diffraction was measured, a spectrum pattern substantially the same as that of Example 1 was obtained.

Example 3

Production of Crystal of 5-Aminolevulinic Acid Phosphate

In 10 mL of purified water was dissolved 5 g of a solid (powder) of 5-aminolevulinic acid phosphate obtained by a conventional method (the method described in Example 1 of WO2005/100300 pamphlet), and then 100 mL of isopropanol was added under stirring. After 5 minutes of stirring at room temperature, the whole was allowed to stand at −25° C. for 17 hours. The precipitated crystal was collected and washed with 50 mL of acetone. It was dried under reduced pressure for 8 hours and 4.68 g of the crystal was collected. When powder X-ray diffraction was measured, a spectrum pattern substantially the same as that of Example 1 was obtained.

Example 4

Production of Crystal of 5-Aminolevulinic Acid Phosphate

In 30 mL of purified water was dissolved 10 g of a solid (powder) of 5-aminolevulinic acid phosphate obtained by a conventional method (the method described in Example 1 of WO2005/100300 pamphlet), and then 89 g of methoxyethanol was added under stirring. After 15 days of standing at room temperature, the precipitated crystal was collected and washed with 50 mL of acetone. It was dried under reduced pressure for 16 hours and 7.01 g of the crystal was collected. When powder X-ray diffraction was measured, a spectrum pattern substantially the same as that of Example 1 was obtained.

Example 5

Production of Crystal of 5-Aminolevulinic Acid Phosphate

The same treatment was conducted as in Example 4 except that acetone was used instead of methoxyethanol, and 6.53 g of a crystal was collected. When powder X-ray diffraction was measured, a spectrum pattern substantially the same as that of Example 1 was obtained.

Example 6

Production of Crystal of 5-Aminolevulinic Acid Phosphate

The same treatment was conducted as in Example 4 except that 1,4-dioxane was used instead of methoxyethanol, and 6.41 g of a crystal was collected. When powder X-ray diffraction was measured, a spectrum pattern substantially the same as that of Example 1 was obtained.

Example 7

Production of Crystal of 5-Aminolevulinic Acid Phosphate

The same treatment was conducted as in Example 4 except that γ-butyrolactone was used instead of methoxyethanol, and 3.09 g of a crystal was collected. When powder X-ray diffraction was measured, a spectrum pattern substantially the same as that of Example 1 was obtained.

Example 8

Production of Crystal of 5-Aminolevulinic Acid Phosphate

The same treatment was conducted as in Example 4 except that triethylene glycol dimethyl ether was used instead of methoxyethanol, and 7.23 g of a crystal was collected. When powder X-ray diffraction was measured, a spectrum pattern substantially the same as that of Example 1 was obtained.

Example 9

Production of Crystal of 5-Aminolevulinic Acid Phosphate

The same treatment was conducted as in Example 4 except that tetraethylene glycol dimethyl ether was used instead of methoxyethanol, and 6.94 g of a crystal was collected. When powder X-ray diffraction was measured, a spectrum pattern substantially the same as that of Example 1 was obtained.

Example 10

Production of Crystal of 5-Aminolevulinic Acid Phosphate

In 30 mL of purified water were dissolved 10.05 g (60.0 mmol) of 5-aminolevulinic acid hydrochloride and 4.5 mL (65.7 mmol) of 85% by mass phosphoric acid, and then 5.83 g (62.7 mmol) of γ-picoline was added dropwise under stirring. After the completion of the dropwise addition, the whole was stirred at room temperature for 10 minutes and then 400 mL of ethanol was added. A precipitated crystal was collected by suction filtration and dried under reduced pressure at room temperature for 19 hours. Thus, 10.55 g (46.1 mmol) of a crystal of 5-aminolevulinic acid phosphate was obtained in a yield of 77% by mol. When powder X-ray diffraction was measured, a spectrum pattern substantially the same as that of Example 1 was obtained.

Test Example 1

Test on Moisture Absorption Resistance

With regard to 5-aminolevulinic acid phosphate, moisture absorption resistance was evaluated by weighing out 1 g of each of the powder obtained by a conventional method (the method described in Example 1 of WO2005/100300 pamphlet) and the crystal obtained in Example 1, allowing it to stand under conditions of 25° C. and 90% RH, subsequently measuring mass after the passage of each period of time, and calculating a ratio of change in mass. The results are shown in Table 2.

TABLE 2

| | 25° C., 90% RH | |
|---|---|---|
| Time passed | Powder | Crystal |
| 1 hr | +6% | +0.05% |
| 3 hr | +11% | +0.06% |
| 5 hr | +14% | +0.09% |
| 6 hr | +16% | +0.08% |
| 7 hr | +17% | +0.09% |
| 24 hr | +21% | +0.4% |

As shown in Table 2, the crystal of the invention was excellent in moisture absorption resistance as compared with the conventional powder.

Test Example 2

Thermal Stability Test

With regard to 5-aminolevulinic acid phosphate, 1 g of each of the powder obtained by a conventional method (the method described in Example 1 of WO2005/100300 pamphlet) and the crystal obtained in Example 1 was weighed out and allowed to stand under each condition shown in Table 3. The amount of 2,5-pyrazinedipropionic acid (PDPA), which is an impurity generated by heating and a compound formed by dimerization of 5-aminolevulinic acid molecules, was measured by liquid chromatography. An increase in the content of PDPA in 5-aminolevulinic acid phosphate was calculated and thermal stability as a substance was evaluated. The results are shown in Table 3.

TABLE 3

| Heating temperature | Heating time | Increase in PDPA concentration in solid | |
| --- | --- | --- | --- |
| | | Powder | Crystal |
| 30° C. | 96 hr | +10 ppm | +0 ppm |
| 60° C. | 96 hr | +302 ppm | −0 ppm |

Analytical conditions for liquid chromatography: separation column: μBondasphere C18 5μ 100 Å manufactured by Waters, eluent: a mixture of 2% aqueous acetic acid solution and methanol in a volume ratio of 90/10, flow rate: 1.0 mL/min, injection amount of sample: 50 μl, column temperature: 40° C., detector: UV detector (276 nm).

As shown in Table 3, the crystal of the invention showed a small increase in PDPA as compared with the case of the conventional powder and thus was excellent in thermal stability.

Test Example 3

Test on Solid State Stability

With regard to 5-aminolevulinic acid phosphate, the melting point of the powder obtained by a conventional method (the method described in Example 1 of WO2005/100300 pamphlet) and the melting point of the crystal obtained in Example 1 were measured by means of a melting point-measuring instrument (manufactured by Yanagimoto Mfg. Co., Ltd.). The results are shown in Table 4.

TABLE 4

| | Powder | Crystal |
| --- | --- | --- |
| Melting point | 108-109° C. | 129-131° C. |

As shown in Table 4, the crystal of the invention had a melting point 20° C. higher than that of the conventional powder and was excellent in thermal stability in a solid state. This fact enables application of common heating sterilization at 121° C.

While the invention has been described in detail and with reference to specific embodiments thereof, it will be apparent to one skilled in the art that various changes and modifications can be made therein without departing from the spirit and scope thereof.

The present application is based on Japanese Patent Application No. 2006-221538 filed on Aug. 15, 2006, and the contents are incorporated herein by reference.

INDUSTRIAL APPLICABILITY

According to the present invention, there can be provided a novel crystal of 5-aminolevulinic acid phosphate having a high thermal stability, a high melting point, and an excellent moisture absorption resistance as well as a process for producing the same.

The invention claimed is:

1. A crystal of 5-aminolevulinic acid phosphate, which shows characteristic peaks at 7.9°±0.2°, 15.8°±0.2°, 18.9°±0.2°, 20.7°±0.2°, 21.1°±0.2°, 21.4°±0.2°, 22.9°±0.2°, 33.1°±0.2°, and 34.8±0.2° as diffraction angles 2θ in powder X-ray diffraction measured with a wavelength of 1.54 Å (Cu Kα), wherein the crystal has a melting point of 129 to 131° C.

2. A process for producing the crystal according to claim 1, wherein a salt of 5-aminolevulinic acid, phosphoric acid, and a basic nitrogen-containing compound are dissolved in a first solvent and then a second solvent having a lower solubility for 5-aminolevulinic acid phosphate as compared with the first solvent is added thereto to precipitate the crystal, wherein the salt of 5-aminolevulinic acid is hydrochloride, hydrobromide, sulfonate, sulfate, or nitrate, and the amount of the basic nitrogen-containing compound is 0.1 to 5 molar equivalents to that of the salt of 5-aminolevulinic acid.

3. The process according to claim 2, wherein the basic nitrogen-containing compound is a pyridine represented by the following formula (1):

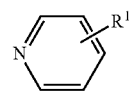

(1)

wherein $R^1$ represents a hydrogen atom, a hydrocarbon group having 1 to 40 carbon atoms which may have a substituent, or an amino group which may have a substituent, or an amine represented by the following formula (2):

$NH_mR^2_{3-m}$ (2)

wherein m represents an integer of 0 to 3 and $R^2$ represents a hydrogen atom or a hydrocarbon group having 1 to 18 carbon atoms which may have a substituent.

4. The process according to claim 2, wherein the second solvent having a lower solubility for 5-aminolevulinic acid phosphate as compared with the first solvent is at least one selected from methanol, ethanol, n-propanol, isopropanol, acetone, γ-butyrolactone, 1,4-dioxane, methoxyethanol, tetraethylene glycol dimethyl ether, and triethylene glycol dimethyl ether.

* * * * *